(12) United States Patent
Suva et al.

(10) Patent No.: US 9,362,094 B2
(45) Date of Patent: Jun. 7, 2016

(54) BIOMARKERS FOR DETERMINING BREAST CANCER BONE METASTASIS

(75) Inventors: Larry Suva, Little Rock, AR (US); Stephanie Byrum, Little Rock, AR (US); Charity Washam, Little Rock, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 455 days.

(21) Appl. No.: 13/825,760

(22) PCT Filed: Sep. 22, 2011

(86) PCT No.: PCT/US2011/052737
§ 371 (c)(1), (2), (4) Date: Jun. 10, 2013

(87) PCT Pub. No.: WO2012/040447
PCT Pub. Date: Mar. 29, 2012

(65) Prior Publication Data
US 2013/0260399 A1 Oct. 3, 2013

Related U.S. Application Data

(60) Provisional application No. 61/385,187, filed on Sep. 22, 2010.

(51) Int. Cl.
*G01N 33/574* (2006.01)
*G01N 33/68* (2006.01)
*H01J 49/00* (2006.01)

(52) U.S. Cl.
CPC ...... *H01J 49/0027* (2013.01); *G01N 33/57415* (2013.01); *G01N 33/6851* (2013.01); *G01N 33/6893* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,530,101 A | 6/1996 | Queen et al. | |
| 5,565,332 A | 10/1996 | Hoogenboom et al. | |
| 5,585,089 A | 12/1996 | Queen et al. | |
| 2004/0013719 A1 | 1/2004 | Holick | |
| 2005/0033023 A1 | 2/2005 | Correale et al. | |
| 2005/0261183 A1 | 11/2005 | Stewart et al. | |

FOREIGN PATENT DOCUMENTS

| | | | |
|---|---|---|---|
| EP | 0 239 400 B1 | 8/1994 | |
| EP | 0 592 106 B1 | 11/2004 | |
| EP | 0 519 596 B1 | 2/2005 | |
| WO | WO 03058198 A2 * | 7/2003 | ....... G01N 33/57415 |
| WO | 2012/040447 A1 | 3/2012 | |

OTHER PUBLICATIONS

Powell et al., Cancer Research, 1991, 51:3059-3061.*
Byrum, The Diagnostic Fingerprint of Breast Cancer Bone Metastasis, A Dissertation Submitted to the Graduated School, University of Arkansas at Little Rock, May 2009.*
Gast et al., Cancer Biomarkers, 2006, 2: 235-248.*
Winden et al., BMC Medical Genomics, 2009, 2:4, 1-14.*
Altschul et al., "Basic Local Alignment Search Tool", J. Mol. Biol., 1990, pp. 403-410, vol. 215.
Altschul et al., "Gapped BLAST and PSI-BLAST: a new generation of protein database search programs", Nucleic Acids Research, 1997, pp. 3389-3402, vol. 25, No. 17.
Amann et al., "Tightly regulated tac promoter vectors useful for the expression of unfused and fused proteins in *Escherichia coli*", Gene, 1988, pp. 301-315, vol. 69.
Cote et al., "Generation of human monoclonal antibodies reactive with cellular antigens", Proc. Natl. Acad. Sci. USA, 1983, pp. 2026-2030, vol. 80.
International Search Report and Written Opinion from related International Application No. PCT/US2011/052737, dated Apr. 3, 2012; 12 pgs.
Karlin et al., "Methods for assessing the statistical significance of molecular sequence features by using general scoring schemes", Proc. Natl. Acad. Sci. USA, 1990, pp. 2264-2268, vol. 87.
Kohler et al., "Pillars Article: Continuous cultures of fused cells secreting antibody of predefined specificity", Nature, 1975, pp. 495-497, vol. 256, No. 5517.
Roguska et al., "Humanization of murine monoclonal antibodies through variable domain resurfacing", Proc. Natl. Acad. Sci. USA, 1994, pp. 969-973, vol. 91.
Studnicka et al., "Human-engineered monoclonal antibodies retain full specific binding activity by preserving non-CDR complementarity-modulating residues", Protein Engineering, 1994, pp. 805-814, vol. 7, No. 6.

* cited by examiner

*Primary Examiner* — Hong Sang
(74) *Attorney, Agent, or Firm* — Polsinelli PC (57) ABSTRACT

The invention provides biomarkers and biomarker profiles that discriminate between a subject with breast cancer that has metastasized to the bone and a subject with breast cancer that has not metastasized to the bone. In particular, the biomarker and biomarker profile include polypeptides present or present at higher levels in the circulatory system of subjects having breast cancer bone metastasis compared to subjects having breast cancer without bone metastasis.

3 Claims, 5 Drawing Sheets
(4 of 5 Drawing Sheet(s) Filed in Color)

```
                         SEQUENCE LISTING

<160> NUMBER OF SEQ ID NOS: 2

<210> SEQ ID NO 1
<211> LENGTH: 111
<212> TYPE: DNA
<213> ORGANISM: Homo sapiens

<400> SEQUENCE: 1
gggaagtcca tccaagattt acggcgacga ttcttccttc accatctgat cgcagaaatc      60
cacacagctg aaatcagagc tacctcggag gtgtcccta actccaagcc c               111

<210> SEQ ID NO 2
<211> LENGTH: 37
<212> TYPE: PRT
<213> ORGANISM: Homo sapiens

<400> SEQUENCE: 2

Gly Lys Ser Ile Gln Asp Leu Arg Arg Arg Phe Phe Leu His His Leu
1               5                   10                  15

Ile Ala Glu Ile His Thr Ala Glu Ile Arg Ala Thr Ser Glu Val Ser
            20                  25                  30

Pro Asn Ser Lys Pro
            35
```

BIOMARKERS FOR DETERMINING BREAST CANCER BONE METASTASIS

FIELD OF THE INVENTION

The present invention generally provides compositions and methods to determine whether breast cancer in a subject has metastasized to the bone. More particularly, the present invention provides biomarkers and a biomarker profile that determine whether breast cancer in a subject has metastasized to the bone.

BACKGROUND OF THE INVENTION

Currently, there are approximately 2 million women in the United States living with breast cancer and the disease is the second leading cause of cancer death in women. Approximately 80% of women with metastatic breast cancer will have tumors arise in the bone. Bone is a common site for cancer metastasis, and bone metastases are frequently associated with complications such as hypercalcemia due to osteolysis, nerve compression, intractable bone pain and pathological fractures. The observation that the majority of cancers exhibit target organ preference when they disseminate was first described in a study of the autopsy records of 735 women who died of breast cancer. The study showed that the highest numbers of metastases were found in the ovaries and the skeleton. The progression of breast cancer bone metastases requires the establishment of functional interactions between metastatic breast cancer cells and bone cells. These interactions are presumably mediated by direct cell-cell contact, and/or soluble stimulators that directly or indirectly induce osteoclast formation and activity.

A critical barrier to understanding and treating breast cancer metastasis and other metastatic cancers is the paucity of sensitive and validated biomarkers. The clinical evaluation of bone metastasis in individual cancer patients involves radiographic confirmation of the diagnosis, the investigation of secondary causes of bone loss and the evaluation of clinical bone turnover biomarkers. However, few bone turnover biomarkers for cancer have been demonstrated to have clinical significance. Therefore, the identification of new target molecules useful in the diagnosis and treatment of cancer and other diseases is a continuing need. In addition, methods for evaluating the role that target molecules play in breast cancer are also needed. In particular, detection of cancer-derived gene products from biologic fluids is an important emerging approach to the diagnosis of malignant diseases.

SUMMARY OF THE INVENTION

Briefly, therefore, one aspect of the disclosure provides a biomarker profile for diagnosing breast cancer bone metastasis in a subject. The biomarker profile is represented by SELDI polypeptide peaks chosen from M4133.27 Da, M4260.92 Da, M4740.39 Da, M11386.2 Da, M11452.8 Da, M 11525.9 Da, M11629.0 Da, M 11679.7 Da, M11728.2 Da, M11894.2 Da, M17384.8, M17577.3 and M39096.5 Da.

In an additional aspect of the disclosure provides a plurality of circulating peptides purified from the plasma of at least one subject diagnosed as having breast cancer bone metastasis. The plurality of circulating peptides are purified by a process comprising obtaining a plasma sample from the subject; determining the SELDI spectra comprising polypeptide peaks from the plasma sample that differentiates breast cancer bone metastasis from breast cancer without bone metastasis; and determining the amino acid sequence of each polypeptide peak in the SELDI spectra.

In yet another aspect, the disclosure provides an isolated nucleic acid that encodes a biomarker that may be used as a means to diagnose whether breast cancer bone metastasis has occurred in a subject. In particular, the nucleic acid is chosen from: a nucleotide sequence consisting of SEQ ID No: 1; a nucleotide sequence that is at least 80% identical to SEQ ID No: 1; a nucleotide sequence that encodes a polypeptide consisting of SEQ ID No: 2; and a nucleotide sequence that encodes a polypeptide consisting of SEQ ID No: 2 with conservative amino acid substitutions. In various iterations of the invention, the nucleic acid sequence may be operably linked to an expression control sequence and inserted into an expression vector.

In a further aspect the disclosure provides a purified polypeptide that is a biomarker that may be used as a means to diagnose whether breast cancer bone metastasis has occurred in a subject. More particularly, the polypeptide is chosen from: an amino acid sequence consisting of SEQ ID No: 2, an amino acid sequence that is at least 80% identical to SEQ ID No: 2, and an amino acid sequence of SEQ ID No: 2 with conservative amino acid substitutions. The invention also includes a purified antibody that binds specifically to the peptide.

Another aspect of the disclosure encompasses use of the polypeptide biomarker in a method to detect breast cancer bone metastasis in a subject. The method comprises obtaining a biological sample from the subject; and determining whether the polypeptide of SEQ ID NO: 2 is present in the biological sample. The presence of the polypeptide indicates that the subject's breast cancer has metastasized to the bone.

In a further aspect, the disclosure provides use of the biomarker profile to detect breast cancer bone metastasis in a subject. The method comprises obtaining a biological sample from the subject; and determining whether the biological sample has the biomarker profile comprising SELDI polypeptide peaks M4260.92 Da, M4133.27 Da, and M4740.39 Da. The presence of the polypeptide peaks indicates that the subject's breast cancer has metastasized to the bone.

Other aspects and iterations of the disclosure are described in more detail below.

DESCRIPTION OF THE FIGURES

The patent or application file contains at least one drawing executed in color. Copies of this patent or patent application publication with color drawing(s) will be provided by the Office upon request and payment of the necessary fee.

FIG. 1 depicts the data analysis protocol using a flow-chart. Training set samples (36 samples) were analyzed using bioinformatic and statistical tools to build a RF training model. Peak information from SELDI TOF-MS spectra from the training set samples was used as a preliminary model. The preliminary model was then used for the validation set to test the samples in a blinded fashion (unknown class, 40 samples) in order to determine the ability of the diagnostic classification scheme to distinguish between two groups of patients, i.e. patients with bone metastasis versus patients without bone metastasis. The two data sets were then combined to determine sensitivity and specificity of the biomarker profile in the RF fingerprint. A diagnostic biomarker profile comprising 13 peaks with higher specificity and sensitivity was then generated, with the level of specificity and sensitivity determined.

FIG. 3 depicts the diagnostic biomarker profile comprising identified and validated SELDI peaks. The final diagnostic biomarker profile was generated from all 76 patient samples. In all, 13 peak variables distinguished between breast cancer patients with (black bars) and without (grey bars) bone metastasis. The median fold changes in the peak intensities were demonstrated by the length of the bars. The 13 significant discriminatory peaks included m/z 4133.27, 4260.92, 4740.39, 11386.2, 11452.8, 11525.9, 11629.0, 11679.7, 11728.2, 11894.2, 17384.8, 17577.3, 39096.5 Da. All of the peaks with the exception of 4740.39Da, 17384.8 Da and 17577.3 Da were found increased in breast cancer patients with bone metastasis.

FIG. 4 depicts the tryptic map of PTHrP(12-48) in peptide identification. The tryptic map of PTHrP(12-48) was shown with the overlapping fragment from PTHrP(1-37). Top panel showed the partially purified patient plasma fraction 5. The m/z 4260 peak was shown by dotted circle in the top panel. Middle panel was the trypsin digestion of fraction 5, and the expected two specific peptide peaks for PTHrP[12-48] were shown in the mid panel (see the arrows). Bottom panel showed the tryptic digestion of PTHrP[1-37], which identified the overlapping and expected peak at 1948.2 Da (see the arrow).

DETAILED DESCRIPTION OF THE INVENTION

The present disclosure is based on the discovery of circulating polypeptides that are present in the plasma of subjects having breast cancer bone metastasis. The same polypeptides are either not present in detectable amounts or detectable only in very low amounts in subjects having breast cancer that has not metastasized to the bone. In this regard, the present disclosure provides a means to diagnose with both sensitivity and specificity subjects that have breast cancer bone metastasis.

(I) Identification of Biomarkers for Breast Cancer Bone Metastasis

The present disclosure provides biomarkers and a biomarker profile that discriminate between subjects that have breast cancer with bone metastasis and subjects that have breast cancer without bone metastasis. The biomarkers were identified via a series of proteomic technologies. Briefly, the proteomic technologies utilize Surface Enhanced Lacer Desorption Ionization (SELDI) Time-of-Flight Mass Spectrometry (TOF-MS) in order to identify a SELDI spectra comprising polypeptide peaks that are present in biological samples taken from subjects that have breast cancer bone metastasis and that are either not present in detectable amounts or detectable only in very low amounts in biological samples taken from subjects that have breast cancer without bone metastasis. Also may be identified by SELDI-TOF MS are olypeptide peaks that are present in biological samples taken from subjects that have breast cancer without bone metastasis and that are either not present in detectable amounts or detectable only in very low amounts in biological samples taken from subjects that have breast cancer bone metastasis. Results from the SELDI profile were then validated using biochemical characterization and mass spectrometry-based identification procedures in concert with bioinformatic and statistical analysis. The manner in which each of these techniques was used to identify the biomarkers and biomarker profile of the invention is fully detailed in the Examples.

One aspect of the disclosure provides a panel of biomarkers that discriminates between subjects that have breast cancer with bone metastasis and subjects that have breast cancer without bone metastasis. The biomarker profile comprises a plurality of circulating polypeptides that have been purified from a plasma sample of at least one subject that has breast cancer bone metastasis. The plurality of polypeptides were purified by a process that comprises: obtaining a plasma sample from at least one subject that has been diagnosed with breast cancer bone metastasis; determining the SELDI spectra comprising polypeptide peaks that differentiates breast cancer bone metastasis from breast cancer without bone metastasis; and determining the amino acid sequence of each polypeptide peak in the SELDI spectra.

Figure 3:
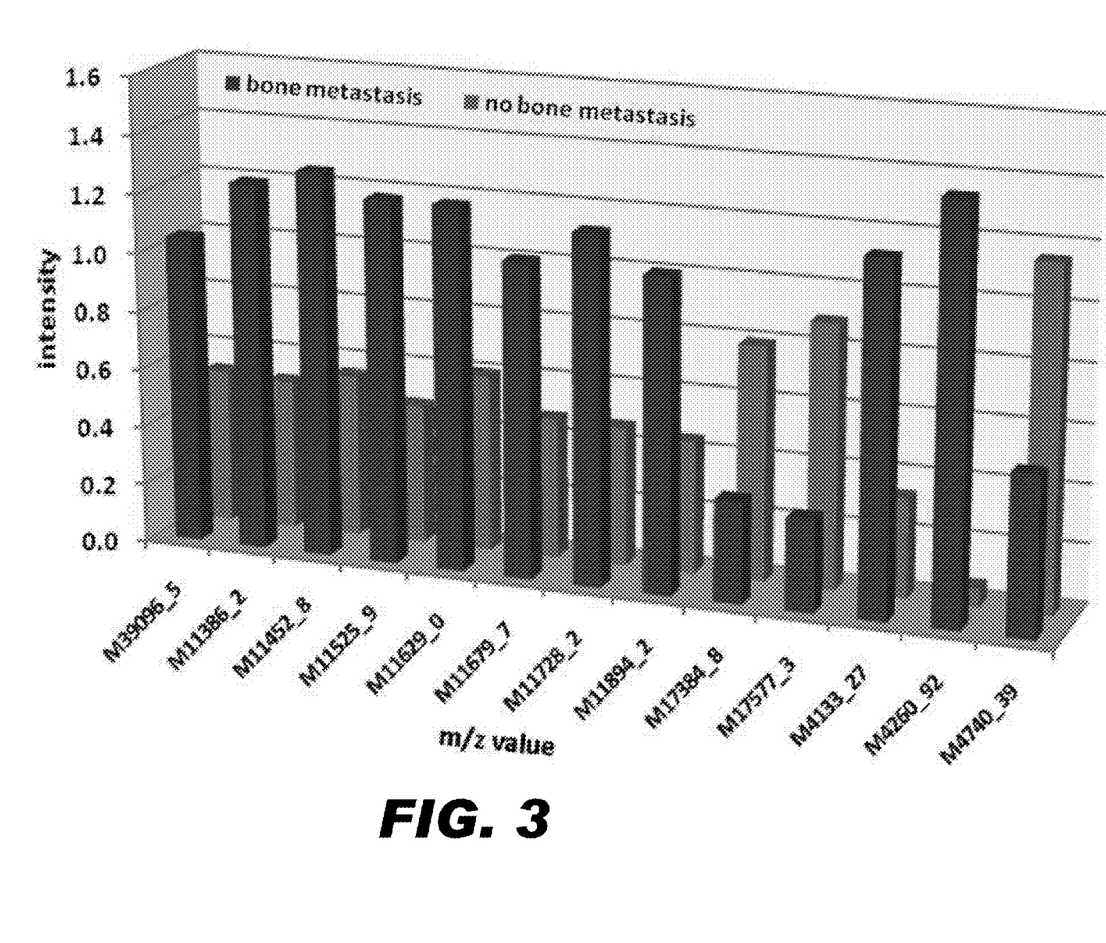

With reference to FIG. 3 and Table 1 detailed in the Examples, a SELDI profile was identified that comprises 13 discrete polypeptide peaks differentiated via their molecular weights. SELDI analysis was done in strict accordance with the protocol described in the Examples. As shown in FIG. 3, with the exception of 4740.39 Da, 1738.4 Da and 17577.3 Da, which were decreased in breast cancer patients with bone metastasis, each of the other 11 polypeptides peaks is present in subjects with breast cancer bone metastasis. In contrast, each of these 11 polypeptides is either present in lower levels or not present in detectable levels in subjects that have breast cancer without bone metastasis. One iteration of the disclosure provides a biomarker profile for breast cancer bone metastasis represented by SELDI polypeptide peaks chosen from M4133.27 Da, M4260.92 Da, M4740.39 Da, M11386.2 Da, M11452.8 Da, M11525.9 Da, M11629.0 Da, M11679.7 Da, M11728.2 Da, M11894.2 Da, and M39096.5 Da. In one exemplary iteration, the biomarker profile is represented by SELDI polypeptide peaks comprising M4260.92 Da, M4133.27 Da, and M4740.39 Da. In a further exemplary iteration, the biomarker profile is represented by the SELDI polypeptide peak M4260.92 Da. As illustrated in the examples, use of the biomarker profile is able to discriminate between breast cancer subjects with bone metastasis and without bone cancer metastasis with 98% sensitivity and 82% specificity.

Another iteration of the disclosure provides polypeptides purified from each of the 13 SELDI peaks detailed in FIG. 3 and Table 1. In one iteration, the polypeptide is purified from peak M4133.27 Da. In another iteration, the polypeptide is purified from peak M4740.39 Da . In another iteration, the polypeptide is purified from peak M11386.2 Da. In a further embodiment, the polypeptide is purified from peak M11452.8 Da. In an additional iteration, the polypeptide is purified from peak M11525.9 Da. In still another embodiment, the polypeptide is purified from peak M11629.0 Da. In an additional iteration, the polypeptide is purified from peak M11679.7 Da. In yet another embodiment, the polypeptide is purified from peak M11728.2 Da. In a further embodiment, the polypeptide is purified from peak M11894.2 Da. In a further embodiment, the polypeptide is purified from peak M17384.8 Da. In a further embodiment, the polypeptide is purified from peak M17577.3 Da. In a further embodiment, the polypeptide is purified from plasma sample fraction containing the polypeptide peak M39096.5 Da. The peptides may be purified via any method generally known in the art of protein biochemistry. For example, the polypeptides may be purified via standard methods include electrophoretic, molecular, immunological and chromatographic techniques, including ion exchange, hydrophobic, affinity, and reverse-phase HPLC chromatography, and chromatofocusing. As another example, the polypeptide may be purified from the flow through of reverse-phase beads. Ultrafiltration and diafiltration techniques, in conjunction with protein concentration may also be used. For general guidance in suitable purification techniques, see Scopes, R., Protein Purification, Springer-Vertag, NY (1982).

After purification from the SELDI polypeptide peak, identification of a selected biomarker peptide peaks can be performed by sequencing the purified proteins. The amino acid sequence of the polypeptide may be determined via methods generally known in the art. For example, the amino acid sequence may be determined via direct determination from X-ray crystal data; Edman degradation, see Stryer, Biochemistry, W. H. Freeman & Co., (1975); cyanogen bromide degradation, trypsin digestion, or staphylococcal protease. These methods can be used either alone, or in combination, or with mass spectrometry techniques, as is well-known in the art. For example, the amino acid sequence may be determined by tryptic peptide mapping using with tandem mass spectrometry on a Q-TOFII system (MicroMass) equipped with a PCI 1000 ProteinChip Tandem MS interface after trypsin digestion.

In an exemplary iteration, the polypeptide is purified from SELDI peak M4260.92 Da in accordance with the method described in the Examples. This polypeptide sequence was also determined in accordance with methods detailed in the Examples and was found to have the amino acid sequence of SEQ ID No: 2 (GKSIQDLRRRFFLHHLIAEIHTAEIRAT-SEVSPNSKP). Analysis of SEQ ID No: 2 revealed that the polypeptide is a circulating fragment of the parathyroid hormone related protein (PTHrP) that is produced in many cancers including breast tumors. The polypeptide fragment of SEQ ID No: 2, also referred to herein as PTHrP (12-48), is the first known time that a fragment from PTHrP has been identified in the systemic circulation. As detailed above, PTHrP (12-48) discriminates between breast cancer with bone metastasis and breast cancer without bone metastasis with a high degree of sensitivity and specificity. The disclosure also includes polypeptides that are 50%, 55%, 60%, 65%, 70%, 80%, 85%, 90%, 95%, and greater than 99% identical to the amino acid sequence of SEQ ID NO: 2. The degree of amino acid sequence identity may be suitably determined by means of computer programs known in the art, such as Vector NTI 10 (Invitrogen Corp.) For pairwise alignment the score used is preferably BLOSUM62 with Gap opening penalty of 10.0 and Gap extension penalty of 0.1. The degree of amino acid sequence identity may also be determined using the BLASTp algorithm of Karlin and Altschul (Proc. Natl. Acad. Sci. USA 87:2264-2268, 1993). The percentage of sequence identity is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which an identical amino acid occurs in both sequences to yield the number of matched positions, dividing the number of matched positions by the total number of positions in the window of comparison and multiplying the result by 100 to yield the percentage of sequence identity.

In still another iteration, the polypeptide may be the amino acid sequence of SEQ ID NO. 2 with conservative amino acid substitutions. Conservative amino acid substitutions, as used herein, include amino acid residues that may be substituted with another amino acid residue having a similar side chain without affecting the function of the peptide. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups include: valine-leucine-isoleucine, phenylalanine-tyrosine, lysine-arginine, alanine-valine, and asparagine-glutamine.

The terms "isolated," "purified" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from open reading frames that flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be 100% pure.

In addition, the disclosure also encompasses the amino acid sequence identified from the SELDI peaks chosen from M4133.27 Da, M4260.92 Da, M4740.39 Da, M11386.2 Da, M11452.8 Da, M11525.9 Da, M11629.0 Da, M11679.7 Da, M11728.2 Da, M11894.2 Da, M17384.8, M17577.3 and M39096.5 Da or amino acids sequences that are 50%, 55%, 60%, 65%, 70%, 80%, 85%, 90%, 95%, and greater than 99% identical to the amino acid sequence of from each of the aforementioned SELDI peaks. The disclosure also encompasses the amino acid sequences from each of the aforementioned SELDI peaks having conservative amino acid substitutions.

The disclosure also encompasses antibodies that specifically bind to any of the polypeptides detailed above, including the polypeptide of SEQ ID NO: 2. The antibody may be polyclonal, monoclonal chimeric, single chain antibodies, a humanized antibody, Fab fragments, and fragments produced by a Fab expression library. Briefly, polyclonal antibodies may be made via methods generally known in the art such as injecting a polypeptide that has immunogenic properties to various hosts, which including goats, rabbits, rats, mice, humans, and others may be immunized by injection. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol.

Monoclonal antibodies may be made via methods generally known in the art such as using a technique that provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:3142; Cote, R. J. et al. (1983) Proc. Natl. Acad. Sci. USA 80:2026-2030; and Cole, S. P. et al. (1984) Mol. Cell Biol. 62:109-120.) Each of the foregoing antibodies may be humanized via methods known in the art, for example, CDR-grafting (EP 239,400; PCT publication WO 91/09967; U.S. Pat. Nos. 5,225,539; 5,530,101 and 5,585,089), veneering or resurfacing (EP 592,106; EP 519, 596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332).

Various detectable labels such as a reporter molecule or enzyme that is capable of generating a measurable signal can be covalently or noncovalently joined to an antibody of the present invention. Typically, the label is detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The disclosure also encompasses nucleic acids that encode any of the forgoing polypeptides, including the polypeptide having SEQ ID NO: 2. In one embodiment, the nucleic acid has the nucleotide sequence of SEQ ID NO: 1 (GGGAAGTC-CATCCAAGATTTACGGCGACGATTCTTC-CTTCACCATCTGATCGC AGAAATCCACACAGCT-GAAATCAGAGCTACCTCGGAGGTGTCCCCTAACTCCAA GCCC). In an additional embodiment, the nucleic acid encodes a polypeptide that has the amino acid sequence of SEQ ID NO: 2 with conservative amino acid substitutions. In an additional embodiment, the nucleotide sequence is at least 50%, 55%, 60%, 65%, 70%, 80%, 85%, 90%, 95%, and greater than 99% identical to the nucleotide sequence of any of the aforementioned nucleic acid sequences. The percent of sequence identity of two nucleic acid sequences or two polypeptides is determined using the algorithm of Karlin and Altschul (Proc. Natl. Acad. Sci. USA 87:2264-2268, 1993). Such an algorithm is incorporated into the NBLAST and XBLAST programs of Altschul et at (J. Mot Biol. 215:403-410, 1990). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention, To obtain gapped alignments for comparison purposes, Gapped BLAST is utilized as described in Altschul et at (Nucleic Acids Res. 25:3389-3402, 1997). When utilizing BLAST and Gapped BLAST programs, the default parameters of the respective programs (e.g., XBLAST and NBLAST) are employed. See ncbi.nlm.nih.gov for more details.

In an additional aspect the disclosure provides expression vectors comprising any of the foregoing nucleic acids operably linked to at least one expression control sequence. Expression vectors containing these nucleic acids are useful to obtain host vector systems to produce proteins and polypeptides. Suitable expression vectors include plasmids, viral vectors, including phagemids, adenoviruses, adeno-associated viruses, retroviruses, cosmids, etc. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. Suitable examples of expression vectors also include inducible non-fusion *E. coli* expression vectors, such as pTrc (Amann et al., (1988) Gene 69:301-315) and pET 11d (Studier et al., Gene Expression Technology: Methods in Enzymology 185, Academic Press, San Diego, Calif. (1990) 60-89). Suitable examples of expression control sequences can and will vary and include a transcriptional or translational control sequences required for expressing the nucleotide sequence. Suitable transcription or translational control sequences include but are not limited to replication origin, promoter, enhancer, repressor binding regions, transcription initiation sites, ribosome binding sites, translation initiation sites, and termination sites for transcription and translation.

(II) Use of Biomarkers to Diagnose Breast Cancer Bone Metastasis

The biomarkers and biomarker profile of the invention may be used to distinguish subjects with breast cancer that have bone metastasis from subjects with breast cancer not having bone metastasis. As detailed in the Examples, use of the biomarkers and biomarker profile described in section (I) discriminate between breast cancer bone metastasis and breast cancer without bone metastasis with a sensitivity of about 98% and a specificity of about 82%. In this vein, the biomarkers and biomarker profile may be effectively used in methods to detect breast cancer bone metastasis.

In one iteration, the biomarkers and biomarker profile are utilized to detect breast cancer bone metastasis in a subject. The method typically comprises two steps: obtaining a biological sample from the subject; and determining whether the polypeptide of SEQ ID NO: 2 is present in the biological sample. In this regard, the presence of the polypeptide indicates that the subject's breast cancer has metastasized to the bone.

In an alternative iteration, the method comprises obtaining a biological sample from the subject; and determining whether the biological sample has the biomarker profile comprising SELDI polypeptide peaks M4260.92 Da, M4133.27 Da, and M4740.39 Da. The presence of the polypeptide peaks indicates that the subject's breast cancer has metastasized to the bone. In each of the foregoing iterations the biological sample may be further analyzed to determine the presence of one or more of the following SELDI polypeptide peaks M11386.2 Da, M11452.8 Da, M 11525.9 Da, M11629.0 Da, M 11679.7 Da, M11728.2 Da, M11894.2 Da and M39096.5 Da. In another foregoing iterations the biological sample may be further analyzed to determine the absence of one or more of the following SELDI polypeptide peaks M17384.8, M17577.3 Da. In addition, for each of the forgoing embodiments, the biological sample may be further analyzed to determine the absence of one or more of M17384.8 and M17577.3 Da, and the presence of an amino acid sequence purified from any of the following SELDI polypeptide peaks M4133.27 Da, M4740.39 Da, M11386.2 Da, M11452.8 Da, M 11525.9 Da, M11629.0 Da, M 11679.7 Da, M11728.2 Da, M11894.2 Da, and M39096.5 Da.

The type of biological sample and the manner in which the sample is collected can and will vary. Numerous types of samples can be obtained from an organism to produce a protein profile. The term "sample" or "biological sample" is used in its broadest sense. The term "subject" is used in its broadest sense and includes several animal species having chemokine receptors. In a preferred embodiment, the subject is a mammal. Non-limiting examples of mammals include humans, dogs, cats, horses, cows, sheep, goats, and pigs. Depending upon the embodiment of the invention, for example, a sample may comprise a bodily fluid which include blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print or any other material isolated in whole or in part from a living subject. Such samples include, but are not limited to, tissue isolated from primates, e.g., humans, or rodents, e.g., mice, and rats. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A biological sample for use is obtained in methods described in this invention. Most often, this will be done by removing a sample from a subject, but can also be accomplished by using previously isolated samples (e.g., isolated by another person, at another time, and/or for another purpose), or by performing the methods of the invention in vivo. Archival tissues, having treatment or outcome history, will be particularly useful.

The means by which the amino acid sequence or the SELDI polypeptide peak is detected and identified also can and will vary. SELDI analysis using training set, validation set, or a combination thereof identifies the primary discriminatory peaks. In addition to relying on the reproducibility in SELDI analyses, a number of algorithms can and may be used to select SELDI peaks by determining the discriminatory power of these peaks. The algorithms known in the art in statistics, bioinformatics and machine learning can and will vary. These algorithms include Analysis of Variance (ANOVA), two-way hierarchiacal clustering, Stepwise Discriminant Analysis (DA), Random Forest (RF), Partial Least Squares (PLS), Partial Least Squares discriminant analysis (PLS-DA), Principle Component Analysis (PCA), See5 Decision Tree and Classification and Regression Tree Analysis (CART).

On-chip tryptic mapping and fragment identification by Matrix-Assisted Laser Desorption Ionization (MALDI), or by bioinformatics analyses and searching in protein databases based on the molecular mass and Ki may also be used for protein identification of the SELDI peak. In one embodiment, MALDI spectra may be used to determine a more accurate molecular weight. MALDI spectra may be collected in the certain molecular weight range, using a PerkinElmerSciex MALDI prOTOF (Perkin Elmer, Waltham, Mass.). In a preferred embodiment, in the range of 1,000 Da to 10,000 Da, the acquisition parameters for MALDI were: laser shots 5,000; laser energy 90%; laser rate 100.0 Hz; with a cooling flow of 150.0 ml/m. The subsequent confirmation and identification of a peptide may be achieved by on-chip tryptic mapping using SELDI. In another embodiment, immunodepletion of the peak using antibody against the preliminarily identified protein of the peak provides biologic confirmation of the peak identity.

Typically, the presence of the amino acid sequence (e.g., SEQ ID NO: 2) or SELDI polypeptide peaks identified above indicate that a subject's breast cancer has metastasized to the bone. As illustrated in FIG. 3, some of the polypeptides are not detectably present in subjects having breast cancer without bone metastasis or if present, the level is significantly lower compared to a subject having breast cancer bone metastasis. Also as illustrated in FIG. 3, some of the polypeptides are not detectably present in subjects having breast cancer with bone metastasis or if present, the level is significantly lower compared to a subject having breast cancer without bone metastasis. As such, depending upon the biomarker, in one embodiment, the presence of the polypeptide purified from peak M4133.27 Da indicates bone metastasis. In another iteration, the presence of the polypeptide purified from peak M11386.2 Da indicates bone metastasis. In a further embodiment, the presence of the polypeptide purified from peak M11452.8 Da indicates bone metastasis. In an additional iteration, the presence of the polypeptide purified from peak M11525.9 Da indicates bone metastasis. In still another embodiment, the presence of the polypeptide purified from peak M11629.0 Da indicates bone metastasis. In an additional iteration, the presence of the polypeptide purified from peak M11679.7 Da indicates bone metastasis. In yet another embodiment, the presence of the polypeptide purified from peak M11728.2 Da indicates bone metastasis. In a further embodiment, the presence of the polypeptide purified from peak M11894.2 Da indicates bone metastasis. In a further embodiment, the decrease of the polypeptide purified from peak M4740.39 Da in comparison to the level of the said polypeptide in breast cancer without metastasis to bone indicates bone metastasis. In a further embodiment, the decrease of the polypeptide purified from peak M17384.8 Da in comparison to the level of the said polypeptide in breast cancer without metastasis to bone indicates bone metastasis. In a further embodiment, the decrease of the polypeptide purified from peak M17577.3 Da in comparison to the level of the said polypeptide in breast cancer without metastasis to bone indicates bone metastasis. In a further embodiment, the presence of the polypeptide purified from plasma sample fraction containing the polypeptide peak M39096.5 Da.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1

Plasma Sample Preparation for SELDI-TOF MS

The identification and independent validation of a diagnostic signature indicative of bone metastasis is the foundation for the identification of biomarkers that assess disease status, progression and/or response to therapy in individual patients. In the expanding application and utility for disease diagnosis, there were concerns regarding the reliability of SELDI-TOF MS in detecting the biochemical changes associated with progressive diseases. These concerns include reproducibility, contributory effects of nonspecific interference by circulatory molecules unrelated to disease state, and the lack of standardization of specimen collection, preparation, and techniques used in detecting differentiating m/z peaks, among others.

In the face of these concerns, the mass spectrometry field has responded with a serious effort to enable access to the relevant data and subsequent validation in independent laboratories, primarily through the Human Proteome Organization Plasma Proteome Project (HUPO PPP). Recent studies demonstrated the reproducible and consistent analysis of serum/plasma across multiple sites using the SELDI platform. MS acquired data have demonstrated a concordance of 97.1% in classifications based on spectra acquired at the two different institutions. These data parallel analyses that have demonstrated the reliability of gene expression profiling. One aspect of the invention is the development of standardized methods for patient selection, sample collection and preparation, sample storage, data collection and data analysis.

Figure 1:
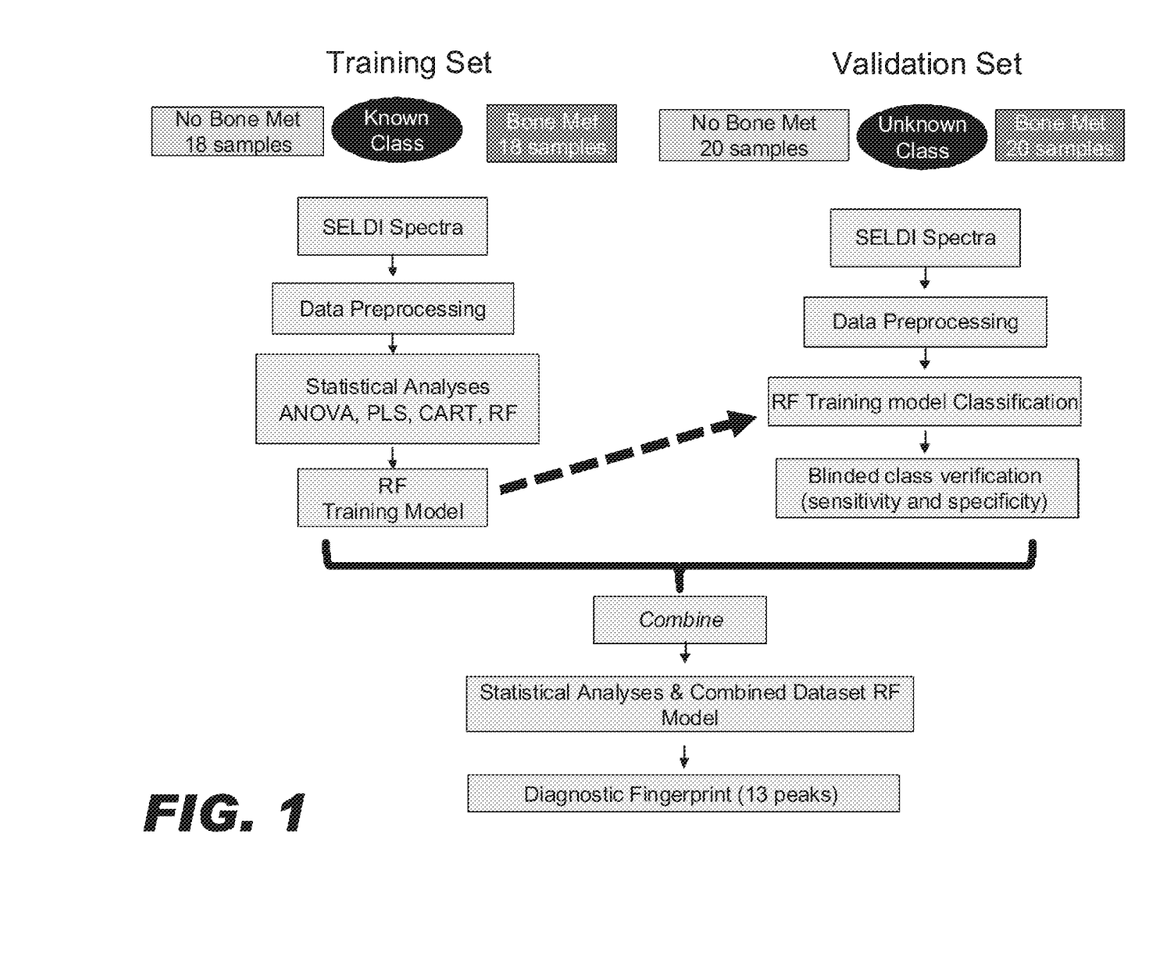

Thirty-six archival plasma samples from well characterized cohorts of breast cancer patients in the collection of the Hershey Medical Center were analyzed. Clinical parameters such as serum biochemical markers of bone turnover, presence of bone and other metastases, survival and time to progression of these 36 samples were collected. These initial breast cancer patient plasma samples were analyzed as a training set, because they were of known class and were selected based on patient bone scans, x-ray evidence, and elevated blood N-Telopeptide (NTx) levels, a clinical marker of bone resorption. Eighteen of the 36 samples of the training set were with bone metastasis, and 18 samples were without metastasis to bone. The second shipment of specimens used as a validation set was received more than a year later and contained 40 plasma samples with unknown class labels (FIG. 1).

The crude plasma samples (10 µl) were diluted 1:5 fold in 9M urea/2% CHAPS (40 µl). Small aliquots (10 µl) of the diluted sample solutions were then applied in duplicate and in a randomized fashion to individual wells of a bioprocessor containing 8-spot CM10 protein chip arrays (Bio-Rad Laboratories). Aliquots of pooled human quality control (QC) plasma from normal healthy individuals were prepared in the same fashion and applied to random locations on each chip to serve as a quality control. All sample handling procedures were performed robotically using the Biomek 2000 liquid handling system (Beckman Coulter) to minimize the introduction of human errors.

Example 2

Discovery of Discriminatory SELDI-TOF MS Protein Peaks

Since many sources of variation exist at all levels of the experimental process, quality control were performed to assess spot, chip, and sample reproducibility. In order to control and assess the reproducibility of the acquired SELDI spectra, quality control samples (pooled plasma from normal healthy individuals) were randomly applied to the chips, and the correlation and coefficient of variation (CV) were calculated. ProteinChip human plasma controls were used to ascertain chip quality. The CV for the human plasma control samples were calculated with SAS 9.2 (Carey, N.C.).

SELDI spectra were collected using a ProteinChip Reader (Protein Biological System II C, Ciphergen) in three molecular weight (MW) ranges, low (1.5-10 kDa), middle (7.0-30 kDa), and high (25-150 kDa). All sample handling procedures were performed robotically using the Biomek 2000 liquid handling system (Beckman Coulter) to minimize the introduction of human errors. Peaks with a signal-to-noise S/N>2.0 that were present in at least 10% of the samples were detected and identified in all spectra using a 0.3% mass window. Each chip included a randomly assigned control sample (pooled plasma from normal healthy individuals) in order to assess inter assay and inter spot variability.

In order to assess intra-sample correlation, duplicate samples were applied robotically to the protein chips in random locations. Pearson and Spearman correlations were calculated for the duplicate samples. The greatest deviation between the two was 0.095. The median value of the Pearson/Spearman Correlation for the training data set was 0.95068 and 0.90788 respectively with an interquartile range of 0.61 to 0.99 and 0.55 to 0.97. The median value of the Pearson/Spearman correlation for the blinded validation data set was 0.962895 and 0.9331 respectively with an inter-quartile range of 0.83 to 0.99 and 0.82 to 0.97. These high median correlation values indicate high spot-to-spot reproducibility. Therefore, for all subsequent data analyses, the spectrum pairs were averaged together on a peak-by-peak basis. The coefficient of variation (CV) was calculated for 103 peaks in the low MW range and 71 peaks in the middle MW range. The average CV for the low range was 6.6%, and 13.4% for the middle MW range. All CVs were well below the accepted range of 10-20% for SELDI direct profiling without fractionation and similar to the CVs we have reported previously.

Figure 2:
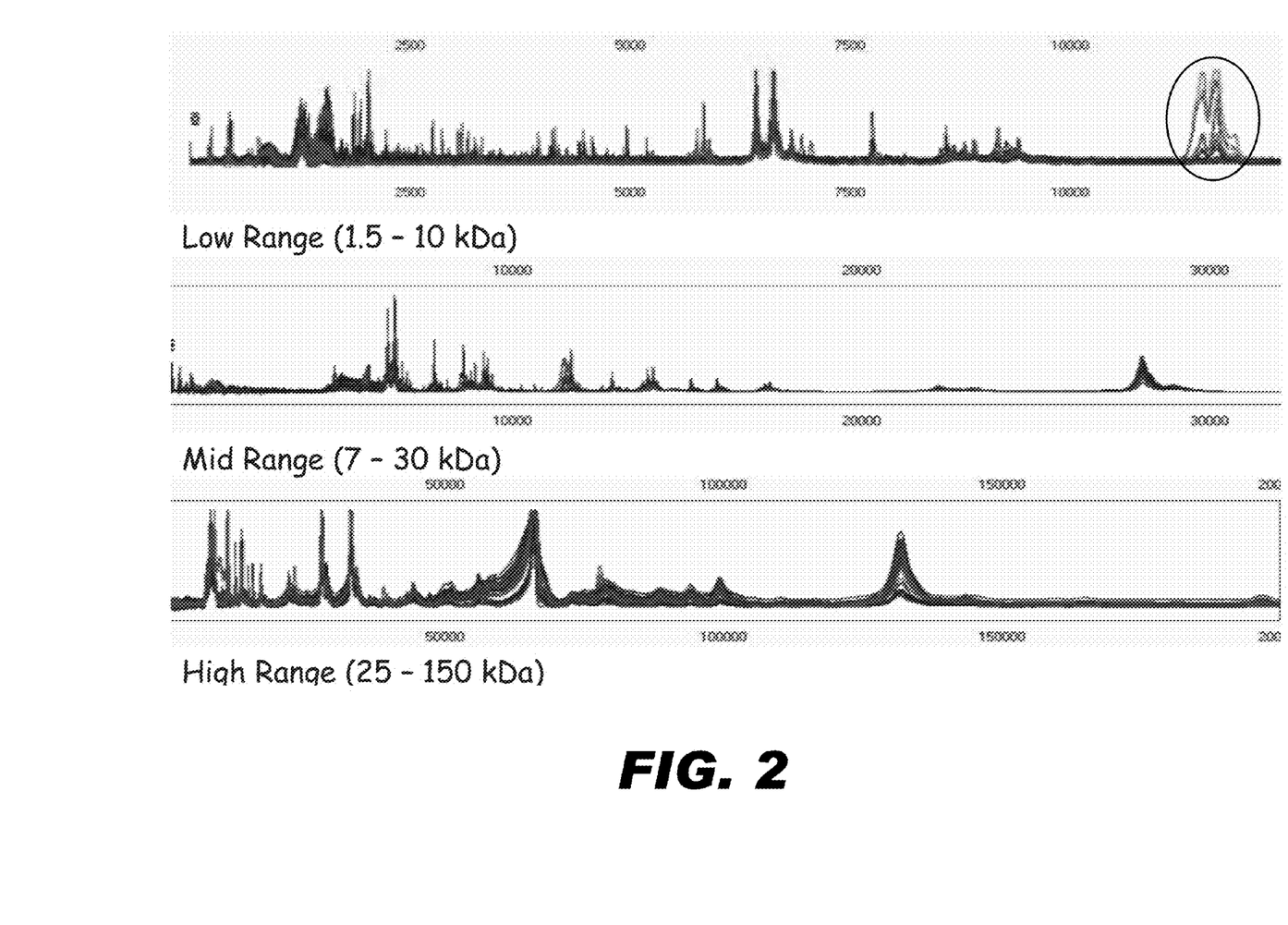
FIG. 2 depicts the reproducibility of SELDI spectra by overlaying the trace view spectrum at each of the Low, Mid and High Range for samples from all patients. The overlaid trace view spectrum enable the visual inspection of the differences between the two patient groups, i.e. patients with bone metastasis (grey) versus patients without bone metastasis (dark). A set of peaks in the 11 kDa range, shown in the circle, was observed with a higher intensity that distinguishes patients of the two groups.

The trace view spectrum for each sample from all patients (FIG. 2) was overlaid to visually inspect the differences between the two patient groups. The samples from bone metastasis (Grey) patients and the samples from patients without bone metastasis (Black) showed clear areas where common peptides were observed, and also areas where the two groups were different. In the 11 kDa range a set of peaks were observed with a higher intensity that distinguishes patients with bone metastasis from the group without bone metastasis. As shown in the FIG. 2, the circled peaks indicating an area of interest, and the same panel of peaks were detected in the overlapping range of both the low range (1.5-10 kDa) and the mid range (7-30 kDa), which represents the reproducibility of the SELDI spectra.

Example 3

Data Analysis and Validation of the Discriminatory SELDI Peaks

Data normalization was performed in two steps. First intra-fraction normalization was applied to the total ion current of m/z ratio in the low and mid molecular weight ranges. Inter-fraction normalization involved the log 2 transformation and then scaling and centering of collected data to mean=0 and STD dev=1. Statistical, bioinformatics, and machine learning analyses were performed to identify a panel of differentially expressed peaks that could distinguish the two patient groups with high sensitivity and specificity. The methods employed included analysis of variance (ANOVA), two-way hierarchical clustering, principal component analysis (PCA), stepwise discriminant analysis (DA), partial least squares discriminant analysis (PLS-DA), See5 decision tree analysis, classification and regression trees (CART), and Random Forest (RF).

As shown by the present invention, a combination of biomarkers was necessary to enhance detection and diagnosis of breast cancer bone metastasis, due to the inherent complexity of the disease. Peaks identified to be significant in multiple analyses were considered more reliable discriminators than those identified by one test alone. Those peaks were used to construct a RF classification model for the early detection of breast cancer bone metastasis in the training set (FIG. 1). The classification scheme (bone or no bone metastasis) in the RF model was verified and the correct class labels were used to calculate the sensitivity and specificity of the model. The RF model containing the classification scheme identified in the training set was then used to classify the independent validation data set in a blinded fashion (FIG. 1). Using the training set RF model, the samples of the validation set were divided into two groups, with 22 samples in the bone metastasis group and 18 samples in the no bone metastasis group. Thus, only two samples (both no bone metastasis i.e. false positives) were misclassified. The validation yielded a sensitivity of 80% and specificity of 70% of the classification scheme using the discriminatory SELDI peaks for the training set.

The training set and the validation set were then combined into a larger dataset, which had a total of 76 samples. The analyses rerun (FIG. 1) of the larger dataset generated a more robust and fully trained RF classification model that discriminates breast cancer patients with and without bone metastasis with high sensitivity (98%) and specificity (82%). In the combined analysis, two additional peaks were identified (m/z 4133 and 4740) that were not components of the original fingerprint. Importantly, all peaks from the training set were identified in the study of the validation set (performed more than 2 years later). Therefore, there were a total of 13 protein peaks discovered in the combined analysis (FIG. 3), and thus a biomarker profile comprising these peaks were identified. These data also confirmed the reproducibility of the approach demonstrated in FIG. 1.

Example 4

Thirteen Significant Protein Peaks in the Diagnostic Biomarker Profile

The final diagnostic fingerprint includes 13 significant peaks that discriminate between breast cancer patients with and without bone metastasis and include m/z 4133.27, 4260.92, 4740.39, 11386.2, 11452.8, 11525.9, 11629.0, 11679.7, 11728.2, 11894.2, 17384.8, 17577.3, 39096.5 Da. All of the peaks with the exception of 17,384.8 and 17577.3 Da were found increased in breast cancer patients with bone metastasis (FIG. 3). The major discriminatory peak in all analyses was determined to be the peptide at mz/4260, which accounted for over 50% of the discriminatory power of the diagnostic biomarker profile comprising the 13 significant protein peaks.

The identification of discriminatory peaks by multiple analyses (Table 1) was the annotation developed for prioritization for protein identification. The primary discriminatory peak observed in the training set for the bone metastasis classification, was also observed as a major discriminating peak in the validation phase. Based on the reproducibility in both SELDI analyses, and the discriminatory power in multiple algorithms, such as Stepwise Discriminant Analysis (DA), Random Forest (RF), Partial Least Squares (PLS), Principle Component Analysis (PCA), See5 Decision Tree and Classification and Regression Tree Analysis (CART), the peak m/z 4260 was prioritized for subsequent identification. Other peaks prioritized for identification (m/z 4133 and m/z 4740) using the same methods were shown in the shaded region in Table 1.

These data demonstrated that a reproducible and biologically relevant multi-protein diagnostic biomarker profile that reflects the progression of breast cancer to bone exists in breast cancer patient plasma. This panel of protein biomarkers can be used to identify osteolytic lesions earlier and with greater accuracy than established techniques. In one embodiment, the biomarker profile is represented by SELDI polypeptide peaks chosen from M4133.27 Da, M4260.92 Da, M4740.39 Da, M11386.2 Da, M11452.8 Da, M 11525.9 Da, M11629.0 Da, M 11679.7 Da, M11728.2 Da, M11894.2 Da, M17384.8, M17577.3 and M39096.5 Da. In another embodiment, the biomarker profile comprising SELDI polypeptide peaks M4260.92 Da, M4133.27 Da, and M4740.39 Da. In yet another embodiment, the diagnosis may be carried out using biomarker represented by the SELDI peak m/z 4260. All of the peaks with the exception of 4740.39 Da, 17384.8 Da and 17577.3 Da were found increased in breast cancer patients with bone metastasis.

TABLE 1

| Peak | ANOVA p-value | Discriminatory Peaks ||||||
|---|---|---|---|---|---|---|---|
|  |  | DA | RF | PLS | PCA | SEE5 | CART |
| M4133.27 | 0.0001 | X | X | X |  |  | X |
| M4260.92 | <0.0001 | X | X | X |  | X | X |
| M4740.39 | 0.0081 | X | X | X |  |  |  |
| M11386.2 | 0.0011 |  | X | X | X |  | X |
| M11452.8 | 0.0009 |  | X | X | X |  | X |
| M11525.9 | 0.0007 |  | X | X | X |  |  |
| M11629.0 | 0.0059 |  | X | X | X |  |  |
| M11679.7 | 0.0094 |  |  | X | X |  | X |
| M11728.2 | 0.0007 | X | X | X |  |  |  |
| M11894.2 | 0.0075 |  | X | X | X |  | X |
| M17384.8 | 0.0494 | X | X |  |  |  |  |
| M17577.3 | 0.0105 |  | X |  |  |  |  |
| M39096.5 | 0.0239 |  |  | X | X |  | X |

Example 5

Protein Purification and Identification

Peaks (m/z 4260.92 Da, 4133.27 Da and 4740.39 Da) were prioritized for identification and sequencing based on their identification by more than one algorithm and appropriate mass (Table 1). Bioinformatics analyses, on-chip tryptic mapping and fragment identification by Matrix-Assisted Laser Desorption Ionization (MALDI) were used to identify the protein in the major discriminatory peak, m/z 4260.92. Based on the molecular mass, Ki and the bioinformatics analysis, the initial search of the protein databases tentatively identified m/z 4260.92 as PTHrP (Parathyroid Hormone related Protein).

To determine a more accurate molecular weight, MALDI spectra were collected in the m/z 1,000 to 10,000 Da molecular weight range, using a PerkinElmerSciex MALDI prOTOF (Perkin Elmer, Waltham, Mass.). The acquisition parameters for MALDI were set up as: laser shots 5,000; laser energy 90%; laser rate 100.0 Hz; with a cooling flow of 150.0 ml/m. This analysis identified the major discriminatory peak (m/z 4260.92Da) as having an actual monoisotopic mass of m/z 4253.3Da. Careful analysis of the PTHrP protein sequence (UniProtKB/Swiss-Prot accession NO. P12272, GeneBank accession No. 17183) identified a single candidate of this molecular weight as a PTHrP peptide that spans residues 12 to 48, which was designated as PTHrP(12-48).

Figure 4:
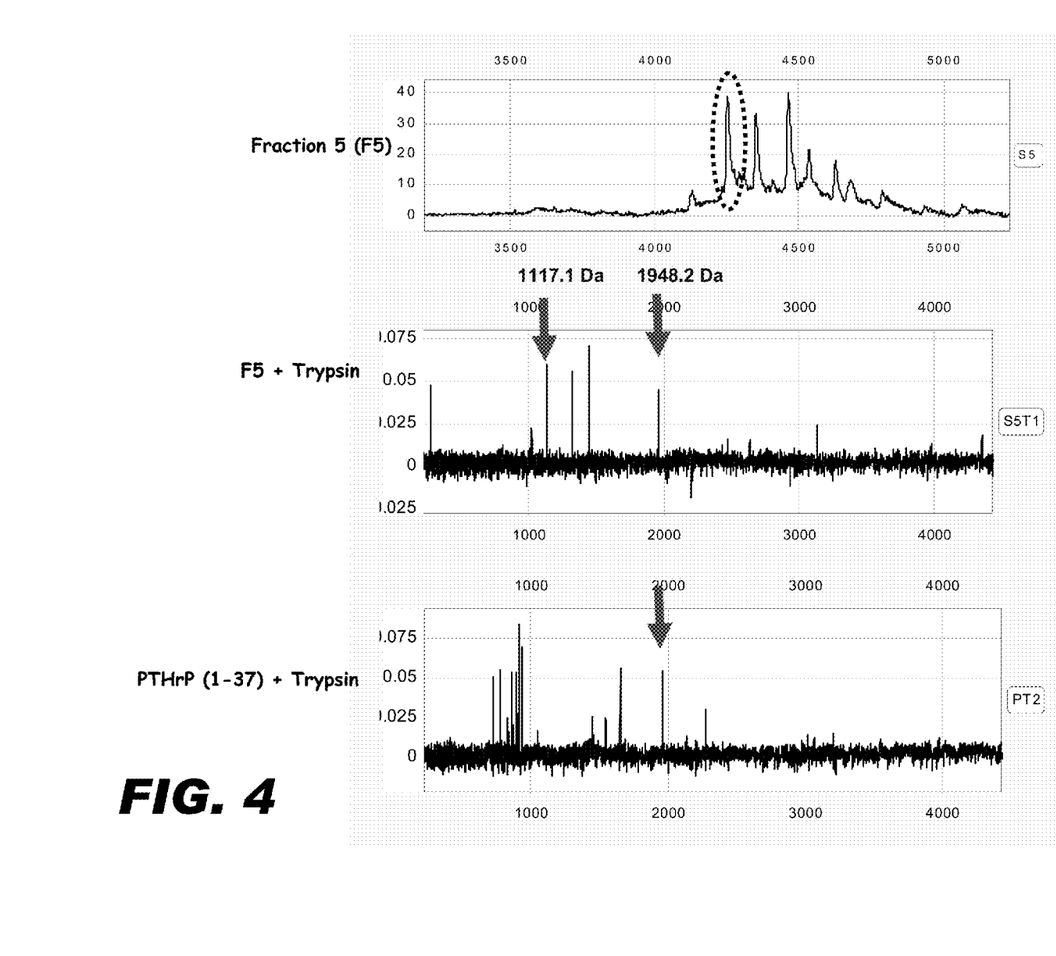
Figure 5:
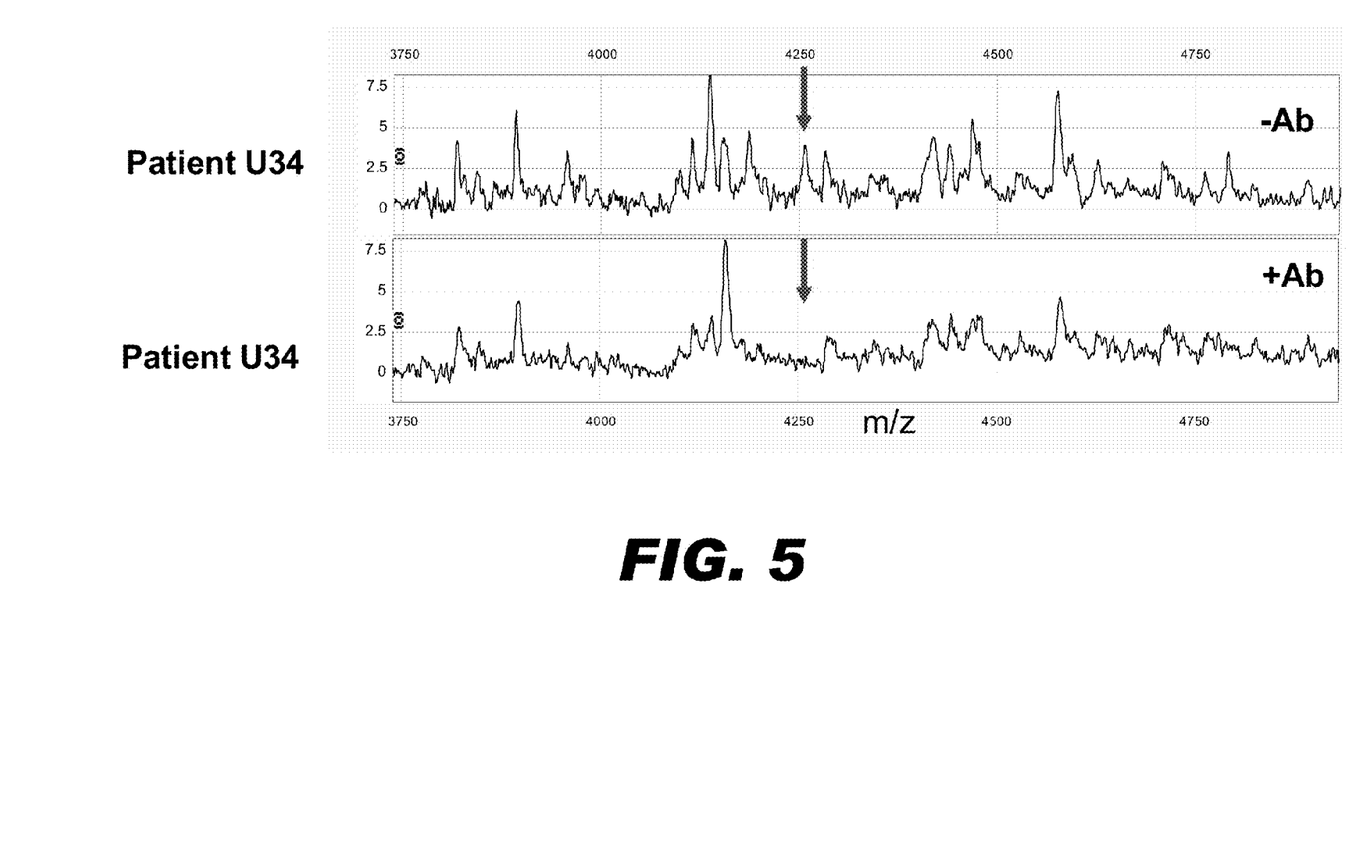
FIG. 5 depicts the immunodepletion of PTHrP(12-48) from patient plasma using the polyclonal antibody of PTHrP (12-48) (PTHrP(12-48) Ab). Patient plasma was treated with PTHrP(12-48) Ab. Arrows identified the position of the peptide peak in plasma in the absence (−Ab) or presence (+Ab) the antibody. As shown in the lower panel, the specific 4253 Da peak was specifically depleted by antibody.

The subsequent confirmation and identification of PTHrP (12-48) as a circulating PTHrP fragment in patient plasma was accomplished by on-chip tryptic mapping using SELDI (FIG. 4). After plasma fractionation, based on biophysical properties, fraction 5 (F5) containing the peak of interest m/z 4260 Da was digested with trypsin. CM10 protein chips were prepared and loaded robotically with 5 µl F5 alone; 5 µl F5+20 ng trypsin; or 2 ng PTHrP+20 ng trypsin all at pH 8.5 in TRIS-HCl. PTHrP alone and trypsin only controls were run as well. Specific peptides corresponding to PTHrP (22-37) and PTHrP (38-48) were identified and are entirely consistent with the identification of the m/z 4253.3 as PTHrP(12-48) from the systemic circulation of breast cancer patients with bone metastasis. Therefore, the major discriminatory protein peak m/z 4253.3 was identified as circulating PTHrP(12-48), the nucleotide sequence of which was set forth by SEQ ID No:1 and the amino acid sequence of which was set forth by SEQ ID No:2. Other peaks present in the analyses are the result of trypsin digestion of the partially purified plasma (FIG. 5). Subsequent analysis by Thermo LTQ-XL ion trap MS confirmed the identity of the PTHrP tryptic peptide m/z 1948.2 Da.

Example 6

PTHrP(12-48) Antibodies

Multiple fragments of human PTHrP that appear to have biologic activities have been described, but none have been shown to circulate or to serve any important physiologically function in vivo. An initial PTHrP(12-48) polyclonal antibody (PTHrP Ab) were developed for further investigation. Patient plasma was treated with PTHrP Ab. The peptide peak in plasma in the absence (−Ab) or presence (+Ab) the antibody was at the position of 4253 Da, as shown by arrow in FIG. 5. This embodiment of the invention, in which the PTHrP(12-48) polyclonal antibody depletes the PTHrP(12-48) peak from patient plasma, provided biologic confirmation of the identity of peptide peak in plasma. This preliminary immunodepletion also confirmed the existence of the peptide in patient plasma. In another embodiment, this antibody may be used in a sensitive enzyme-linked immunosorbent assays (ELISAs) for detection of PTHrP(12-48).

What is claimed is:

1. A method for detecting breast cancer bone metastasis in a subject with breast cancer, the method comprising:
    a. obtaining a biological sample from the subject;
    b. determining whether the plasma sample has the biomarker profile comprising SELDI polypeptide peaks M4260.92 Da, M4133.27 Da, and M4740.39 Da using SELDI-TOF mass spectrometry, and
    c. identifying the subject as having bone metastasis levels of the when SELDI polypeptide peaks M4260.92 Da, M4133.27 Da are increased and SELDI polypeptide peak M4740.39 Da is decreased in the sample as compared to the levels of M4260.92 Da, M4133.27 Da, and M4740.39 Da in a beast cancer subject without bone metastasis.

2. The method of claim 1, further comprising detecting one or more of the SELDI polypeptide peaks selected from the group consisting of M11386.2 Da, M11452.8 Da, M 11525.9 Da, M11629.0 Da, M 11679.7 Da, M11728.2 Da, M11894.2 Da, and M39096.5 Da.

3. The method of claim 1, further comprising detecting the absence of one or more of the SELDI polypeptide peaks selected from the group consisting of M17384.8 and M17577.3.

* * * * *